United States Patent [19]

Crutchfield et al.

[11] 4,092,348

[45] May 30, 1978

[54] OCTASODIUM-1,1,2,2,4,4,5,5-CYCLOHEXANE OCTACARBOXYLATE AND COMPOSITIONS AND METHODS EMPLOYING SAME

[75] Inventors: Marvin M. Crutchfield, St. Louis County; Charles J. Upton, Ballwin, both of Mo.

[73] Assignee: Monsanto Company, St. Louis, Mo.

[21] Appl. No.: 774,171

[22] Filed: Mar. 3, 1977

[51] Int. Cl.[2] .............................................. C07C 61/08

[52] U.S. Cl. ............................ 260/514 K; 252/89 R; 252/132; 252/180; 252/DIG. 11; 260/501.17

[58] Field of Search ........ 260/514 K, 514 LA, 501.17

[56] References Cited

U.S. PATENT DOCUMENTS 3,459,670 8/1969 Carter .................................. 252/99

*Primary Examiner*—Robert Gerstl

*Attorney, Agent, or Firm*—S. M. Tarter; E. P. Grattan; F. D. Shearin

[57] ABSTRACT

This disclosure relates to:

(a) Compounds having the molecular structure represented by the formula:

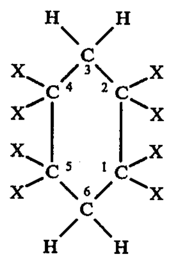

wherein X = COOM, where M is alkali metal, ammonium or trialkanolamine, and preferably is sodium;

(b) solid and liquid detergent compositions incorporating compounds of a) supra, and (c) processes for washing comprising the use of compounds of a) and compositions of b), supra.

2 Claims, No Drawings

OCTASODIUM-1,1,2,2,4,4,5,5-CYCLOHEXANE OCTACARBOXYLATE AND COMPOSITIONS AND METHODS EMPLOYING SAME

BACKGROUND OF THE INVENTION

The invention relates to alkali metal and especially the octasodium 1,1,2,2,4,4,5,5-cylcohexaneoctacarboxylates, detergent formulations comprising such compounds, and the use of such compounds as detergent builders, metal chelants and thresholding agents. The invention also relates to the use of such compounds and compositions in washing processes.

The compounds have utility in complexing various metal ions, such as calcium ions and magnesium ions which contribute to hardness in water. The compounds have shown themselves to be particularly effective in selectively sequestering magnesium ions in the presence of calcium ions. When incorporated in detergent compositions the compounds improve the cleaning ability of the compositions. Thus the principal uses of the compounds are in water treatment, e.g., for water softening and as detergency builders and/or thresholding agents in association with detergent compounds or compositions, particularly when control of magnesium ions is desired.

DESCRIPTION OF THE PRIOR ART

Considerable attention has recently been directed to the development of non-phosphorus detergent builders as partial or total replacements for phosphorus builders, such as sodium tripolyphosphate (STP). Investigators have studied certain polycarboxylates and U.S. Pat. No. 3,704,320 issued Nov. 28, 1972 and U.S. Pat. application Ser. No. 736,962, each in the name of Kent P. Lannert and assigned to the assignee of this application, describe polycarboxylates useful as detergent builders and having the molecular structures represented by the following formulae:

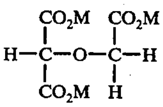
(U.S. Pat. No. 3,704,320)

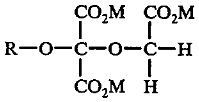
(U.S. Pat. Appln Ser. No. 736,962)

wherein M is generally H, lower alkyl, alkali metal or ammonium and R is alkyl.

In addition, the present two inventors have jointly investigated certain cyclic polycarboxylates of the following general formulae, as to which U.S. patent applications are in the process of preparation:

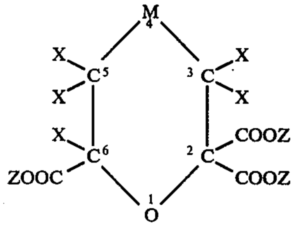
[D-4541]

wherein M is O or $CY_2$, where Y is H or lower alkyl ($C_1$ to $C_4$), X is selected from the group consisting of H, lower alkyl ($C_1$ to $C_4$), or COOZ, and Z represents H, R or one of the salts forming ions from the group alkali metal, ammonium, or trialkanolammonium and R is an alkyl group (branched or straight chain) having up to about $C_{20}$ in the chain;

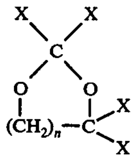
[D-4403]

where X is selected from the group consisting of H, $CCl_3$, and COOZ, where Z represents H, R or one of the salt forming ions from the alkali metal group, or ammonium or trialkanol amine, R is an alkyl group (branched or straight chain) having up to about 20 carbon atoms in the chain, and *n* is 1 or 2.

We are also aware that German Pat. No. 1,168,162 describes cyclohexane-1,2,3,4,5,6-hexacarboxylate and U.K. Pat. No. 1,216,699 describes substantially the same process and the use of the product as a plasticizer.

The present compounds are structurally readily distinguishable from the above-identified compounds and moreover have been found to sequester both calcium and magnesium ions, and surprisingly to be especially effective in sequestering magnesium ions in the presence of calcium ions, a unique property that is quite useful.

SUMMARY OF THE INVENTION

In brief, the invention relates to compounds whose molecular structures are represented by the following general formula:

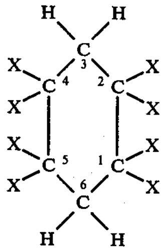

wherein X is COOM, where M is an alkali metal, ammonium or trialkanolamine ion, and preferably is sodium.

The compounds may be synthesized by following the route described by Gregory and Perkin, J. Chem. Soc., 83, 780 (1903) to obtain the octaethyl ester which then may be converted to the octa-salt form by hydrolysis. An alternate route to the synthesis of the octa-ester has also been described by Buzby, Jr., Castro and Reid in J. Org. Chem., 28, 1082 (1963).

The procedure for producing the preferred compound of the invention may generally be illustrated by the reactions set forth below:

$$2X_2CH_2 + H_2CO \rightarrow (X_2CH-)_2-CH_2$$

$$(X_2CH-)_2-CH_2 + 2Br_2 \rightarrow (X_2CBr-)_2-CH_2$$

$$(X_2CBr-)_2-CH_2 + (X_2CH-)_2-CH_2 \xrightarrow[2CH_3CH_2ONA]{}$$

-continued

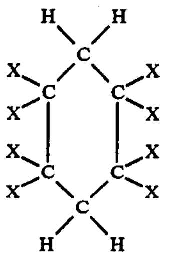

and,

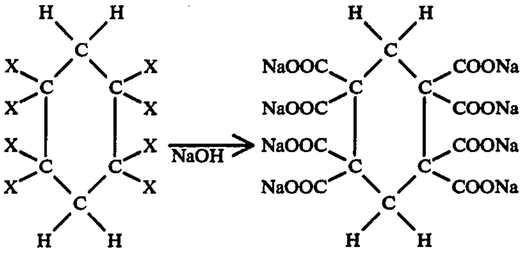

The compounds of the invention find particular utility in sequestering magnesium and are highly effective when added as a builder component to detergent formulations. In particular, the compounds are valuable when added to detergent compositions together with other builders which bind or sequester calcium ions strongly but are less effective in sequestering magnesium ions. For example, detergent compositions containing both the present compounds and the polycarboxylates described in U.S. Pat. No. 3,704,320, supra, compare favorably with STP in overall sequestration of calcium and magnesium ions.

The compositions of the invention comprise various standard solid or liquid detergent compositions containing an amount of the above-described compounds or mixtures of such compounds sufficient to enhance the cleaning capacity of the detergent by providing a building, threshold or other function.

Methods for using the compounds of the invention comprise: 1) softening water by contacting hard water with the compounds of the invention in an amount and for a time sufficient to remove, usually by chelating or sequestering, certain metal ions present in the water, or to complex ions so that they are not available to interfere with soap or detergent compositions added to the water; 2) washing soil articles by contacting the articles with detergent compositions containing or used in the presence of one or more of the compounds of the invention, the compounds being used in amounts sufficient to build or otherwise enhance the cleaning action of the detergent compositions.

DETAILED DESCRIPTION OF THE INVENTION

A. Compounds

The compounds of the invention have the molecular structure represented by the following formula:

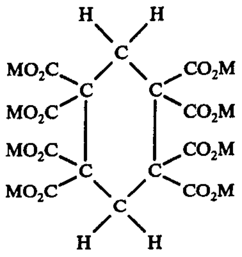

wherein M is an alkali metal, ammonium, or trialkanolamine ion, and preferably is a sodium ion.

B. Methods for Synthesizing the Compounds

The preparation of the compounds may best be understood by reference to the following detailed examples:

(a) Preparation of Tetraethyl-1,1,3,3-Propanetetracarboxylate

The named compound was prepared in the following manner, which is a slight modification of the procedure described by Welch, J. Chem. Soc., 673 (1931).

Diethyl malonate, 360 g. (2.25 mol) and paraformaldehyde 33.8g (1.13 mol) in 200 ml. toluene were treated with 2.0 ml. of a 1.0 molar solution of sodium ethoxide in ethanol. The mixture was heated to 120° over a 1.5 hour period and water was removed as the toluene azeotrope and collected in a Dean Stark trap. The mixture was stirred for 2.5 additional hours at 120°, then treated with 2.0 ml. of 2.8 molar hydrochloric acid in ethanol followed by 10 ml. absolute ethanol. The mixture was then stirred at 25° overnight.

Sodium sulfate (50g) was then added to remove any residual water and after stirring for 15 minutes was removed by filtration. The mixture was then distilled in vacuo yielding 23.9g (7%) recovered diethyl malonate and 270g (72%) of desired tetraethyl 1,1,3,3-propanetetracarboxylate.

(b) Preparation of 1,3-Dibromo-tetraethyl-1,1,3,3-propanetetracarboxylate

The named compound was prepared in the following manner:

A solution of 30g (0.09 mol) of purified tetraethyl-1,1,3,3-propanetetracarboxylate in 100 ml chloroform was placed in a 250 ml flask equipped with a reflux condenser, magnetic stirrer and heating mantle. The flask was irradiated with a sunlamp (275 watt) placed one foot away. A solution of bromine, 33g (0.21 mol) in chloroform, 10 ml was then added dropwise. The reaction was initially spontaneous and exothermic causing reflux and vigorous HBr evolution. However, when half of the bromine had been added, the reaction subsided and was kept at reflux with external heating while the remainder of the bromine was added. The mixture was refluxed until no further HBr was evolved (about 4 hours) and cooled. The mixture was washed with consecutive 100 ml portions of water, 1M sodium metabisulfite, water, sodium bicarbonate solution, water, saturated sodium chloride then dried over magnesium sulfate.

Concentration on the rotary evaporator left 44.5g of a brown viscous oil that slowly solidified. Purification was accomplished by dissolving in 250 ml boiling hexane and treating twice with charcoal (Norit). Concentrating to 100 ml and cooling slowly gave 29.5g, 70% of white crystals.

(c) Preparation of Octaethyl-1,1,2,2,4,4,5,5-cyclohexaneoctacarboxylate

The named compound was prepared in the following manner:

Sodium metal, 1.6g (0.069 mol) was dissolved in 60 ml of absolute ethanol. Then after cooling in an ice bath, 10.8g (0.032 mol) of tetraethyl-1,1,3,3-propanetetracarboxylate in 15 ml absolute ethanol was added. After stirring for 10 minutes, 15.4g (0.031 mol) of 1,3-dibromo-tetraethyl-1,1,3,3-propanetetracarboxylate was added in one portion. Sodium bromide precipitated almost immediately, and after stirring 10–15 minutes at 10°, the mixture was refluxed for 0.5–1 hour and poured into 700 ml ice-water. After 1 hour with intermittent stirring the product was filtered and vacuum dried, giving 17.5g (0.026 mol) 85% of the product. Analysis by gas/liquid phase chromotography (GLPC) and proton magnetic resonance (PMR) indicated the product to be greater than 95% pure. Further purification of the product can be achieved by recrystallization from low boiling petroleum ether.

(d) Preparation of Octasodium-1,1,2,2,4,4,5,5-cyclohexaneoctacarboxylate

The named compound was prepared in the following manner:

Octaethyl-1,1,2,2,4,4,5,5-cyclohexaneoctacarboxylate, 7.2g (0.0109 mol) was hydrolyzed with 21 ml of 5.0 molar aqueous sodium hydroxide (0.105 mol - 20% excess) at 60° for 16 hours. The mixture was cooled and carefully concentrated on a rotary evaporator to remove ethanol.

The aqueous solution (ca. 40 ml) was then added dropwise to 300 ml methanol to precipitate the salt. The product was isolated by filtration, washed with methanol and ether and dried in vacuo overnight. This left 6.9g (0.0106 mol) 97% of white free-flowing solid shown by PMR to be the desired salt, existing as a 4–5 hydrate. Traces of residual base and other trace impurities may be removed by redissolving in water, filtering and reprecipitating with methanol, filtering and vacuum drying.

Ammonium, triethanolamine, other soluble alkali metal salts and the acid form of the cyclic tricarboxylate compounds of this invention are prepared by passing an aqueous solution of the corresponding sodium salt through a column of cationic exchange resin charged with the hydrogen ion, followed by neutralization of the acid with the desired alkali metal hydroxide or amine, and recovering the salt from the solution by evaporation or crystallization.

C. Compositions Comprising the Compounds of the Invention

In detergency builder applications, the use of the alkali metal salts of the compounds, particularly the sodium salt, is preferred. However, in some formulations (such as liquid formulations where greater builder solubility is required) the use of ammonium or alkanol ammonium salts may be desirable.

The detergent formulations will contain at least 1% by weight and preferably at least 5% by weight of the salt forms of compounds of this invention. In order to obtain the maximum advantages of the builder compositions of this invention, the use of from 5% to 75% of these salts is particularly preferred. The salt compounds of this invention can be the sole detergency builder or these compounds can be utilized in combination with other detergency builders which may constitute from 0 to 95% by weight of the total builders in the formulation. By way of example, builders which can be employed in combination with the novel salt compounds of this invention include water soluble inorganic builder salts such as alkali metal polyphosphates, i.e., the tripolyphosphates and pyrophosphates, alkali metal carbonates, borates, bicarbonates and silicates and water soluble organic builders including amino polycarboxylic acids and salts such as alkali metal nitrilotriacetates, cycloalkane polycarboxylic acids and salts, ether polycarboxylates, alkyl polycarboxylates, epoxy polycarboxylates, tetrahydrofuran polycarboxylates such as 2,3,4,5 or 2,2,5,5-tetrahydrofuran tetracarboxylates, benzene polycarboxylates, oxidized starches, amino(-trimethylene phosphonic acid) and its salts, diphosphonic acids and salts (e.g., methylene diphosphonic acid; 1-hydroxy ethylidene diphosphonic acid) and the like.

Particularly valuable builder combinations comprise mixtures of the sodium salts of the compounds of this invention and

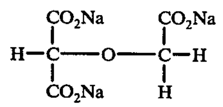

described in the above-mentioned U.S. Pat. No. 3,704,320 - Lannert.

The detergent formulations will generally contain from 5% to 95% by weight total builder (although greater or lesser quantities may be employed if desired) which, as indicated above, may be solely the builder salt compounds of this invention or mixtures of such compounds with other builders. The total amount of builder employed will be dependent on the intended use of the detergent formulation, other ingredients of the formulation, pH conditions and the like. For example, general laundry powder formulations will usually contain 20% to 60% builder; liquid dishwashing formulations 11% to 12% builder; machine dishwashing formulations 60% to 90% builder. Optimum levels of builder content as well as optimum mixtures of builders of this invention with other builders for various uses can be determined by routine tests in accordance with conventional detergent formulation practice.

The detergent formulations will generally contain a water soluble detergent surfactant although the surfactant ingredient may be omitted from machine dishwashing formulations. Any water soluble anionic, nonionic, zwitterionic or amphoteric surfactant can be employed.

Examples of suitable anionic surfactants include soaps such as the salts of fatty acids containing about 9 to 20 carbon atoms, e.g., salts of fatty acids derived from coconut oil and tallow; alkyl benzene sulfonates — particularly linear alkyl benzene sulfonates in which the alkyl group contains from 10 to 16 carbon atoms; alcohol sulfates; ethoxylated alcohol sulfates; hydroxy alkyl sulfonates; alkenyl and alkyl sulfates and sulfonates; monoglyceride sulfates; acid condensates of fatty acid chlorides with hydroxy alkyl sulfonates and the like.

Examples of suitable nonionic surfactants include alkylene oxide (e.g., ethylene oxide) condensates of mono and polyhydroxy alcohols, alkyl phenols, fatty acid amides, and fatty amines; amine oxides; sugar derivatives such as sucrose monopalmitate; long chain tertiary phosphine oxides; dialkyl sulfoxides; fatty acid amides (e.g., mono or diethanol amides of fatty acids containing 10 to 18 carbon atoms), and the like.

Examples of suitable zwitterionic surfactants include derivatives of aliphatic quaternary ammonium compounds such as 3-(N,N-dimethyl-N-hexadecyl ammonio)propane-b 1-sulfonate and 3-(N,N-dimethyl-N-hexadecyl ammonio)-2-hydroxy propane-1-sulfonate.

Examples of suitable amphoteric surfactants include betains, sulfobetains and fatty acid imidazole carboxylates and sulfonates.

It will be understood that the above examples of surfactants are by no means comprehensive and that numerous other surfactants are known to those skilled in the art. It will be further understood that the choice and use of surfactants will be in accordance with well understood practices of detergent formulation. For example, anionic surfactants, particularly linear alkyl benzene sulfonate are preferred for use in general laundry formulations, whereas low foaming nonionic surfactants are preferred for use in machine dishwashing formulations.

The quantity of surfactant employed in the detergent formulations will depend on the surfactant chosen and the end use of the formulation. In general, the formulations will contain from 5% to 50% surfactant by weight, although as much as 95% or more surfactant may be employed if desired. For example, general laundry powder formulations normally contain 5% to 50%, preferably 15% to 25% surfactant; machine dishwashing formulations 0.5% to 5%; liquid dishwashing formulations 20% to 45%. The weight ratio of surfactants to builder will generally be in the range of from 1:12 to 2:1.

In addition to builder and surfactant components, detergent formulations may contain fillers such as sodium sulfate and minor amounts of bleaches, dyes, optical brighteners, soil anti-redeposition agents, perfumes and the like.

In machine dishwashing compositions the surfactant will be a low-foaming anionic or preferably, nonionic surfactant which will constitute 0 to 5% of the formulation.

The term "low-foaming" surfactant connotes a surfactant which, in the foaming test described below, reduces the revolutions of the washer jet-spray arm during the wash and rinse cycles less than 15%, preferably less than 10%.

In the foaming test, 1.5 grams of surfactant is added to a 1969 Kitchen-Aid Home Dishwasher, Model No. KOS-16, manufactured by Hobart Manufacturing Company which is provided with means for counting revolutions of the washer jet-spray arm during wash and rinse cycles. The machine is operated using distilled water feed at a machine entrance temperature of 40° C. The number of revolutions of the jet-spray arm during the wash and rinse cycles is counted. The results are compared with those obtained by operation of the machine using no surfactant charge and the percentage decrease in the number of revolutions is determined.

The surfactant should, of course, be compatible with the chlorine containing component hereinafter discussed. Examples of suitable nonionic surfactants include ethoxylated alkyl phenols, ethoxylated alcohols (both mono- and di-hydroxy alcohols), polyoxyalkylene glycols, aliphatic polyethers and the like. The widely commercially utilized condensates of polyoxypropylene glycols having molecular weights of from about 1400 to 2200 with ethylene oxide (the ethylene oxide constituting 5 to 35 weight percent of the condensate) are, for example, advantageously used in the machine dishwashing formulations of this invention.

Suitable low foaming anionic surfactants include alkyl diphenyl ether sulfonates such as sodium dodecyl diphenyl ether disulfonates and alkyl naphthalene sulfonates.

Mixtures of suitable low-foaming surfactants can be utilized if desired.

In addition, machine dishwashing formulations will contain sufficient chlorine providing compound to provide 0.5% to 2% available chlorine. For example, the formulation may contain from 0.5% to 5%, preferably 1% to 3% of a chlorocyanurate or from 10% to 30% chlorinated trisodium phosphate. Suitable chlorocyanurates are sodium and potassium dichlorocyanurate; [(monotrichloro)tetra-(monopotassium dichloro)] penta-isocyanurate; (monotrichloro) (monopotassium dichloro) diisocyanurate.

Machine dishwashing compositions should additionally contain from 5% to 30% soluble sodium silicate having an $SiO_2$ to $Na_2O$ mole ratio of from 1:1 to 3.2:1 preferably about 2.4:1 to inhibit corrosion of metal parts of dishwashing machines and provide over-glaze protection to fine china.

Machine dishwashing compositions will generally contain at least 10%, preferably at least 20% builder, up to a maximum of about 90% builder. The new salt compounds of this invention should constitute at least 5% of the weight of the machine dishwashing formulation.

As mentioned above, the compounds of the invention, especially the octasodium-1,1,2,2,4,4,5,5-cyclohexaneoctacarboxylates, are effective in binding or sequestering magnesium ions and therefore are particularly useful in combination with other builders which strongly sequester calcium.

The superior magnesium ion sequestration of octasodium-1,1,2,2,4,4,5,5-cyclohexaneoctacarboxylate makes it possible to improve the detergency performance of detergent compositions in which $Mg^{2+}$ binding is otherwise poor by using some of the compound as part of the builder formulation.

The favorable results of using a builder composed of the octasodium compound of the invention plus another builder component having good calcium ion binding efficiency but relatively low magnesium ion binding efficiency were demonstrated by carrying out divalent ion titration of aqueous solutions containing $Ca^{2+}/Mg^{2+}$ in a ratio of 2:1 and a concentration of 100 ppm total hardness, i.e., total $Ca^{2+}$ plus $Mg^{2+}$ which reflects realistically the hardness ion distribution frequently encountered in everyday household laundry washing operations.

The Divalent Electrode Test Procedure for measuring the binding capacity of detergent builders for single divalent cations by an electrode titration method is described by E. A. Matzner et al in an article entitled "Organic Builder Salts as Replacements for Sodium Tripolyphosphate (I)" published in TENSIDE, Vol. 10, 1973, Nos. 3 and 5, pp. 119-125 and 239-245.

A synergistic effect is observed when octasodium-1,1,2,2,4,4,5,5-cyclohexaneoctacarboxylate is used in combination with other builders which preferably bind calcium ion. For example, zeolites as well as many other ether carboxylate builders show a strong preference for calcium ion.

We have found by the use of divalent ion membrane electrodes to monitor free divalent metal ion concentrations, that in solutions containing mixed metal ions of calcium to magnesium of about 2:1, typical of hard tap water, mixtures of the octasodiumcyclohexane-octacarboxylate of the present invention and the previously referred to builder:

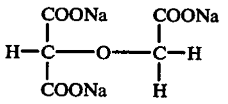

reduce the total divalent ion concentration to desirably lower levels than is possible by the use of either builder alone. Such data suggests a truly cooperative synergistic interaction among the mixed builders and the mixed metal ions. This effect is also detected in the following detergency evaluations.

Octasodium-1,1,2,2,4,4,5,5-cyclohexanepolycarboxylate (Builder 1) was tested for detergency in a standard test in which the reflectivity of washed and unwashed samples of laundry are measured optically on a reflectometer and recorded as Δ Rd, or difference in reflectivity. Higher Δ Rd values are indicative of superior cleaning performance. In this test, the sodium compound of the invention performed 92% as effectively as STP on cotton and 94% as effectively as STP on permanent press/polyester/cotton with an average overall detergency performance of 93% of STP on fabrics soiled with synthetic sebum soil.

The sodium compound of the invention also showed better particulate soil removal performance than:

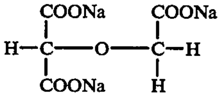

(Builder 2)

when compared in a test for particulate soil removal.

The compound of the present invention was also treated for detergency as a 50/50 blend with Builder 2 and as a 50/50 blend with a zeolite, Type A builder. The 50/50 blend of Builder 1 and Builder 2 performed 99% as effectively as STP on cotton, and 100% as effectively as STP on permanent press polyester/cotton for an overall detergency of 104% of STP. In the same test, Builder 1 and Builder 2 used alone recorded an overall detergency of 93% and 90% of STP, respectively. Thus, the synergistic sequestration observed with mixtures of Builders 1 and 2 is also evident in detergency evaluations. The 50/50 blend of the sodium compound of the invention with zeolite gave an overall average detergency of 84% of STP.

Biodegradation studies on the sodium compound of the invention indicates that the compound biodegrades in about three weeks, a result confirmed by the synthesis of biodegradation of a sample labeled with carbon-14 in which the evolution of radioactive carbon dioxide was detected.

The overall results clearly support the efficacy of the subject compounds as suitable biodegradable, non-phosphorous substitutes for phosphorus-containing builders such as STP.

What is claimed is:

1. Compounds having the molecular structure represented by the formula:

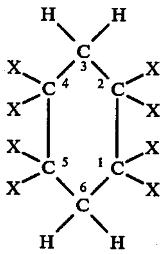

wherein X = COOM, where M is alkali metal ammonium or trialkanolamine.

2. The compound of claim 1 wherein M is sodium.

* * * * *